Figure 1:
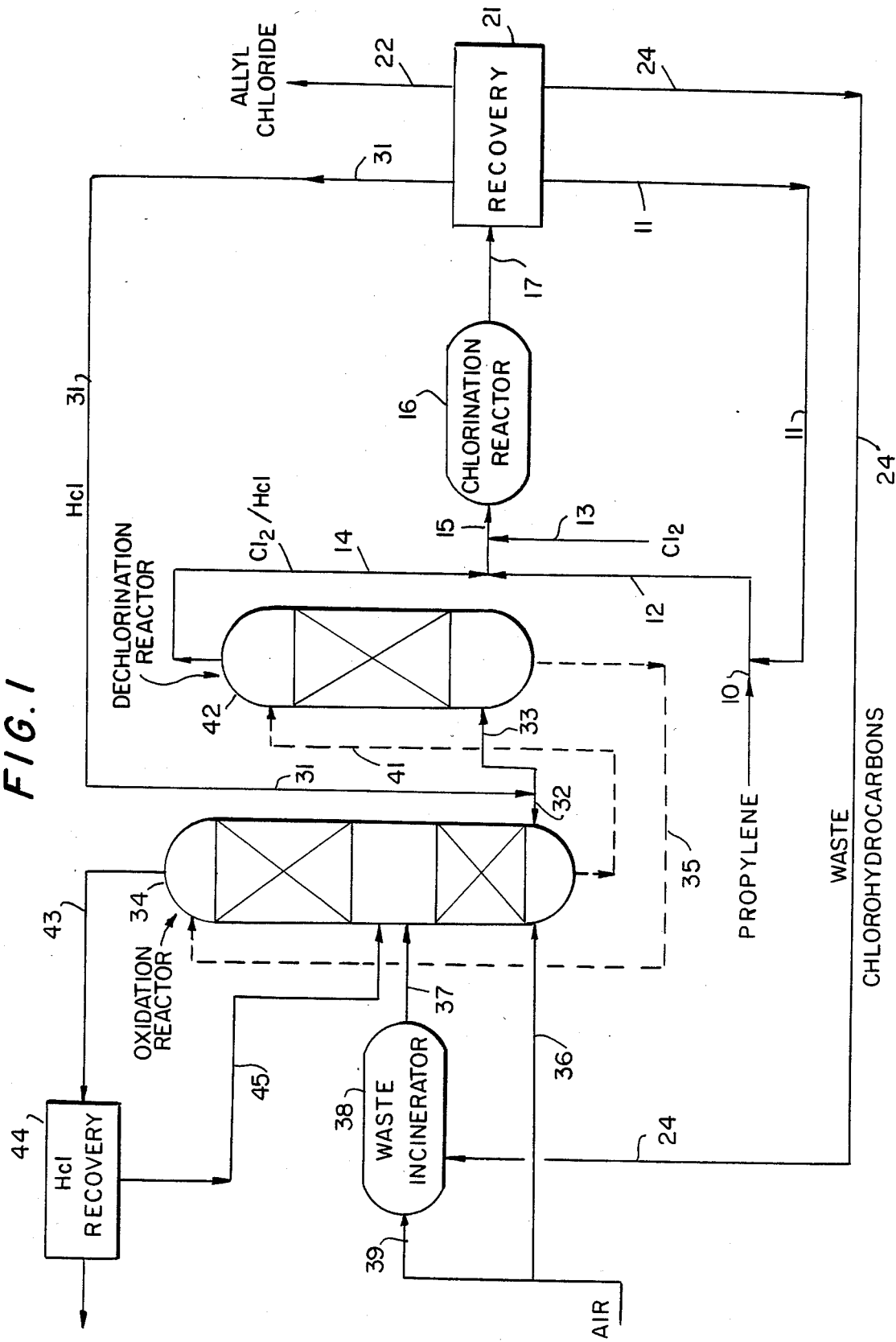

United States Patent [19]

Riegel et al.

[11] Patent Number: 4,558,167

[45] Date of Patent: Dec. 10, 1985

[54] HYDROGEN CHLORIDE-PROPYLENE SEPARATION

[75] Inventors: Herbert Riegel, Maplewood; Chiung-Yuan Huang; Vincent A. Strangio, both of Glen Ridge, all of N.J.

[73] Assignee: The Lummus Company, Bloomfield, N.J.

[21] Appl. No.: 519,250

[22] Filed: Aug. 1, 1983

[51] Int. Cl.⁴ ............................................. C07C 21/067
[52] U.S. Cl. .......................................... 570/238; 203/9; 203/67; 423/488; 570/230; 570/246; 570/262
[58] Field of Search ................. 423/488; 570/230, 238, 570/246, 262; 203/67, 9

[56] References Cited

U.S. PATENT DOCUMENTS

| | | | |
|---|---|---|---|
| 2,227,953 | 1/1941 | Baehr et al. | 423/488 |
| 2,615,791 | 10/1952 | Raley | 423/488 |
| 3,120,568 | 2/1964 | Brown | 570/238 |
| 3,865,886 | 2/1975 | Schindler et al. | 570/238 |
| 4,168,210 | 9/1979 | Boozalis et al. | 423/488 |

OTHER PUBLICATIONS

Perry and Chilton, *Chemical Engineers' Handbook*, 5th ed., pp. 13–43, 44 (1980).

*Primary Examiner*—William R. Dixon, Jr.
*Assistant Examiner*—Steven Capella
*Attorney, Agent, or Firm*—Elliot M. Olstein

[57] ABSTRACT

Hydrogen chloride is recovered from a mixture with propylene by extractive distillation with an inert extraction solvent to minimize reaction between hydrogen chloride and propylene during such distillation. The temperature and pressure conditions are coordinated with the extraction solvent and amount thereof to prevent the presence of hydrogen chloride in a liquid state. The process is particularly suitable for recovering hydrogen chloride in the production of allyl chloride by thermal chlorination of propylene.

12 Claims, 2 Drawing Figures

HYDROGEN CHLORIDE-PROPYLENE SEPARATION

This invention relates to recovery of hydrogen chloride from a mixture containing hydrogen chloride and propylene. This invention further relates to a process for recovering hydrogen chloride in a process directed to the production of allyl chloride by thermal chlorination of propylene.

Hydrogen chloride is generally recovered from a gaseous mixture containing hydrogen chloride by absorbing the hydrogen chloride in water. Thus, for example, in the production of allyl chloride by thermal chlorination of propylene, the effluent contains, in addition to allyl chloride product and chlorinated byproducts, unreacted propylene, and a significant amount of hydrogen chloride byproduct. In general, such hydrogen chloride is separated from the propylene by water absorption of hydrogen chloride to produce hydrochloric acid. The propylene is then dried and recycled to the chlorination reaction. The hydrochloric acid byproduct of the process may be sold if there is a demand for such acid.

In some commercial situations, it is economically impractical to sell such aqueous hydrogen chloride, and as a result there is a necessity to separately recover hydrogen chloride byproduct.

The present invention is directed to effectively recovering hydrogen chloride from a mixture which contains both hydrogen chloride and propylene.

In accordance with one aspect of the present invention, there is provided a process for recovering hydrogen chloride from a mixture containing hydrogen chloride and propylene wherein the mixture is extractively distilled in the presence of an inert extraction solvent which preferentially dissolves propylene to recover hydrogen chloride. as light ends and propylene and extraction solvent as heavy ends. The term "inert" as used herein means that under the distillation conditions the solvent does not react with either propylene and/or hydrogen chloride.

In accordance with a preferred embodiment, the extractive distillation temperature and pressure is coordinated with the extraction solvent and amount thereof such that during the distillation the hydrogen chloride is present only as a gas.

Applicant has found that by employing such extractive distillation, it is possible to separate hydrogen chloride from a mixture, which contains propylene, without significant reaction between hydrogen chloride and propylene, which reaction produces isopropylchloride. Thus, applicant has found that in attempting to employ a conventional fractionation process for recovery of hydrogen chloride from a mixture containing hydrogen chloride and propylene, there is a significant reaction between hydrogen chloride and propylene, which is wasteful of both propylene and hydrogen chloride. Moreover, such reaction is exothermic, which would increase the load on the overhead condenser, and could also result in a runaway exotherm. By using extractive distillation in accordance with the present invention, there is little, if any, reaction between the propylene and hydrogen chloride.

More particularly, the extraction solvent is comprised of a saturated hydrocarbon, and/or halo- substituted saturated hydrocarbon and/or halo- substituted unsaturated hydrocarbon, with the solvent preferably being a saturated hydrocarbon or chloro- substituted derivative thereof. The extraction solvent should have a boiling point which is greater than the boiling point of both the hydrogen chloride and propylene. As representative examples of preferred extraction solvents, there may be mentioned saturated aliphatic hydrocarbons having from 3 to 12 carbon atoms, as well as chloro- substituted saturated hydrocarbons having from 1 to 6 carbon atoms. It is to be understood that other solvents which preferentially dissolve propylene and which are non-reactive under the conditions of extractive distillation are also suitable.

The extraction solvent is employed in such extractive distillation in an amount which is effective to reduce and/or eliminate reaction between propylene and hydrogen chloride during the distillation, i.e. the amount of solvent is selected such that at the distillation temperature and pressure the hydrogen chloride, in the column, is present only as a gas. In general, the extraction solvent is employed in amounts which can vary from 10 to 90 mol percent; and most generally in amounts from 20 to 50 mol percent.

The extractive distillation is conducted at a temperature and pressure effective for separating hydrogen chloride from propylene, with the hydrogen chloride being recovered as the light ends or overhead, and the propylene being recovered in the heavy ends or bottoms. In general, the extractive distillation is conducted at an overhead temperature in the order of from $-100°$ F. to 70° F., a bottoms temperature in the order of from 0° to 200° F., and at a pressure in the order of from 2 atm (abs.) to 40 atm (abs.). As hereinabove noted, the temperature and pressure of the extractive distillation is coordinated with the solvent and amount thereof in a manner such that hydrogen chloride is not present as a liquid during the extractive distillation. Applicant has found that the avoidance of a liquid condition for hydrogen chloride in the distillation column aids in minimizing the reaction between propylene and hydrogen chloride.

It is to be understood that the separation of hydrogen chloride from a mixture containing propylene and hydrogen chloride is not limited to mixtures containing only the two components in that the invention is also applicable to mixtures which contain other components. Thus, for example, the invention has particular applicability to recovering hydrogen chloride from an allyl chloride production effluent, which effluent includes in addition to hydrogen chloride and propylene, allyl chloride, and other chlorinated $C_3$ hydrocarbons.

In employing the present invention for recovery of hydrogen chloride from mixtures containing other components, in accordance with a preferred embodiment, the extractive distillation solvent is one which is indigenous to the process. Thus, for example, in a process directed to the production of allyl chloride, it is possible to employ dichloropropane by-product as an extraction solvent.

The present invention will be further described with respect to a process for the production of allyl chloride which employs molten salts for recovery and reutilization of hydrogen chloride byproduct. The process of the present invention has particular applicability to such a process as a result of the presence of high volumes of hydrogen chloride in the allyl chloride production effluent.

Figure 2:
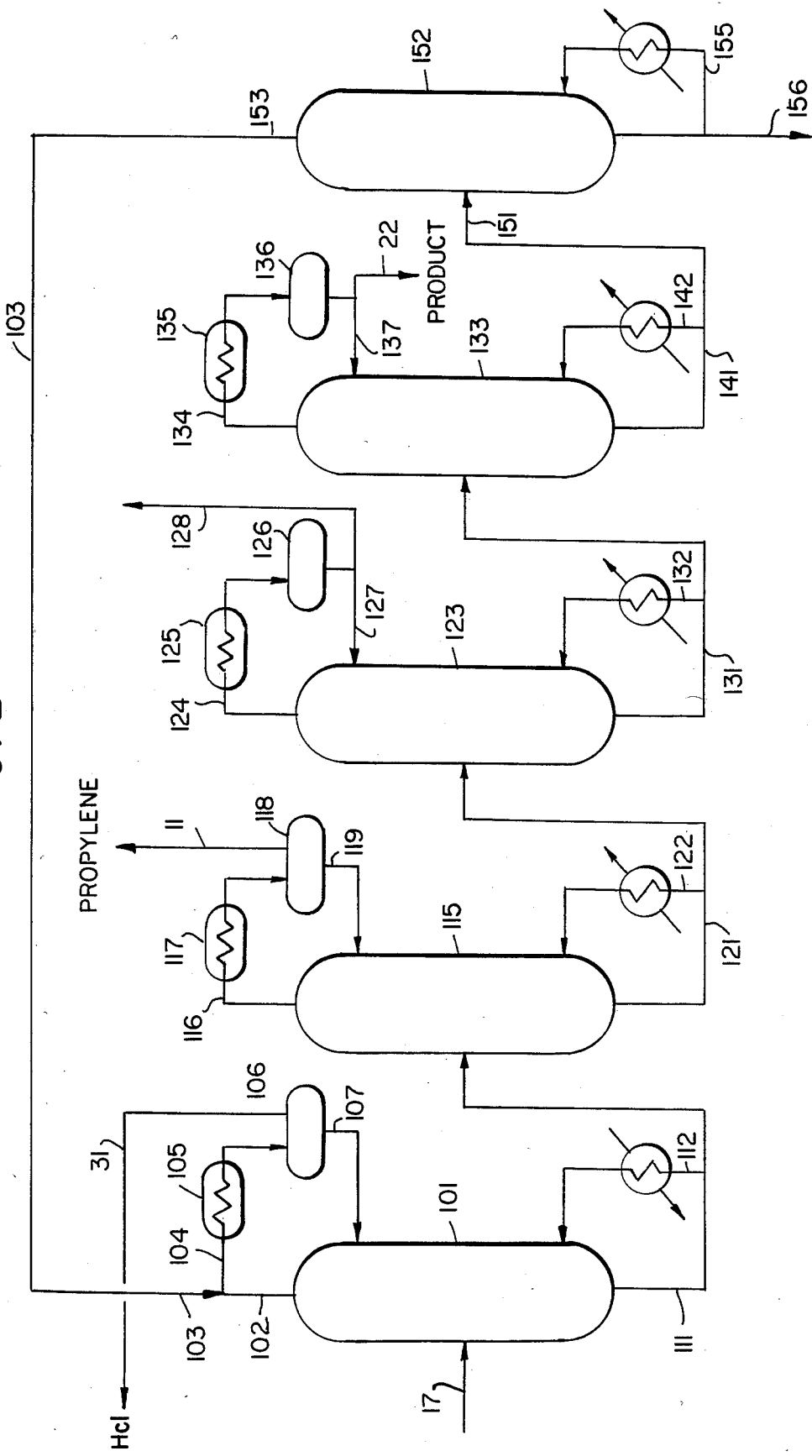

The embodiment of such a process is shown in the accompanying drawings, wherein:

FIG. 1 is a simplified schematic flow diagram of an overall process for producing allyl chloride, which incorporates the present invention; and FIG. 2 is a simplified schematic flow diagram of the recovery portion of the process, which incorporates the present invention.

It is to be understood, however, that the scope of the invention is not to be limited to the embodiment described with reference to the drawings.

Referring now to the drawings, and in particular FIG. 1 thereof, propylene to be chlorinated, in line 10 is combined with recycle unreacted propylene in line 11, and the combined stream in line 12 is combined with fresh feed chlorine in line 13 and a dechlorination reaction effluent in line 14, containing chlorine and hydrogen chloride, and obtained as hereinafter described. The combined stream in line 15 is introduced into a chlorination reactor, schematically generally indicated as 16.

In chlorination reactor 16, the propylene is chlorinated by direct contact with chlorine to produce allyl chloride, hydrogen chloride byproduct as well as other chlorinated $C_3$ compounds. The hydrogen chloride introduced with the feed does not react in the chlorination reactor.

A chlorination reactor effluent, containing allyl chloride, hydrogen chloride byproduct, as well as unreacted feed and other byproducts is withdrawn from reactor 16 through line 17 and introduced into a recovery zone, schematically generally indicated as 21. As hereinafter described in more detail with respect to FIG. 2 of the drawings, in recovery zone 21, hydrogen chloride is recovered through line 31, allyl chloride product is recovered through line 22, recycle propylene is recovered through line 11 and chlorinated hydrocarbon byproducts are recovered through line 24 for treatment as hereinafter described.

The hydrogen chloride recovered from zone 21 in line 31 is split into two portions, one portion of which is the net hydrogen chloride produced in the chlorination reactor 16, in line 32, and the other portion, in line 33, being the portion employed as stripping gas for the dechlorination reactor, which is ultimately introduced into the chlorination reactor 16. The net hydrogen chloride line 32 is introduced into an oxidation reactor, schematically indicated as 34 for effecting recovery thereof.

The oxidation reactor 34 is provided through line 35 with a molten salt mixture containing the higher and lower valent chloride of a multivalent metal, and further including a melting point depressant, such as a mixture of cuprous chloride, cupric chloride and potassium chloride, and is further provided with an oxygen containing gas, such as air through line 36. A chlorinated hydrocarbon combustion effluent, containing hydrogen chloride and some chlorine is also introduced into reactor 34 through line 37. Such effluent is obtained by burning the chlorinated byproducts in line 24 in a combustion zone 38 which is provided with air through line 39.

As a result of the contact between the hydrogen chloride, air, and molten salt, the hydrogen chloride is recovered by enriching the cupric chloride content of the molten salt. In addition, any gaseous chlorine present in the effluent in line 37 is recovered by enriching the cupric chloride content of the molten salt.

A gaseous effluent is withdrawn from reactor 34 through line 43, and such gaseous effluent may include equilibrium amounts of hydrogen chloride, steam and chlorine, if any, as well as components introduced with the combustion effluent in line 37, such as carbon oxides, and with the air, such as nitrogen. The effluent in line 43 may be further treated in the hydrogen chloride recovery zone 44, as known in the art, in order to recover aqueous hydrogen chloride in line 45 which is recycled to the oxidation reactor 34. Thus, for example, such effluent in line 39 may be further treated as described in U.S. Pat. No. 3,968,200.

A molten salt, now enriched in cupric chloride, is withdrawn from reactor 34 through line 41 and introduced into the top of a dechlorination reactor, schematically generally indicated as 42. The dechlorination reactor 42 is operated as hereinabove described in order to strip chlorine from the salt. The dechlorination reactor is provided with hydrogen chloride stripping gas through line 33, and as a result of the conditions in reactor 42 and the stripping action of the hydrogen chloride, gaseous chlorine is stripped from the salt, with the cupric chloride being converted to cuprous chloride.

Molten salt withdrawn from reactor 42 is recycled to reactor 34 through line 35.

A dechlorination effluent, containing gaseous chlorine, as well as hydrogen chloride, introduced as stripping gas, is withdrawn from reactor 42 through line 14, for introduction into the chlorination reactor 16. The chlorine stripped from the salt is that produced from the hydrogen chloride generated in reactor 16, as well as any chlorine values recovered from waste chlorinated product produced in the chlorination reactor 16.

As hereinabove described, the mixture of chlorine and hydrogen chloride stripping gas is preferably directly employed for the chlorination reaction; however, the effluent from the dechlorination reactor 42 may be treated to separately recover the chlorine for introduction into the chlorination reactor 16.

Referring now to FIG. 2 which illustrates the recovery Section 21 of the process, effluent recovered from the chlorination reactor, in line 17, is introduced into an extractive distillation tower, schematically generally represented as 101, for the purpose of separating hydrogen chloride from the effluent. The extractive distillation is preferably conducted by the use of 1,2-dichloropropane, as extraction solvent, in that such material is indigenous to the process. Such dichloropropane is introduced into the tower by introduction of the solvent into the tower overhead, as hereinafter described.

The extractive distillation tower 101 is operated at temperatures and pressures as hereinabove described. The temperature, pressure, solvent and amount thereof are coordinated in a manner such that in tower 101 the hydrogen chloride is not present in liquid form. Gaseous hydrogen chloride overhead is withdrawn from column 101 through line 102, combined with extraction solvent in line 103, obtained as hereinafter described, and the combined stream in line 104 is passed through overhead condenser 105 into a gas-liquid separation vessel 106. Liquid extraction solvent is withdrawn from the vessel 106 through line 107 for introduction into tower 101. Gaseous hydrogen chloride is removed from separation vessel 106 through line 31 for further processing, as hereinabove described.

A bottoms stream is withdrawn from column 101 through line 111, and a portion thereof is employed for meeting reboil requirements through line 112. The effluent in line 111, which contains allyl chloride product, propylene, extraction solvent, as well as chlorinated $C_3$ byproducts is introduced into a column 115 designed and operated to separate propylene from the remaining components.

Propylene overhead is withdrawn from column 115 through line 116, and passed through a suitable overhead condenser into a gas-liquid separator 118. Reflux requirements are provided to the tower through line 119 and, net propylene is withdrawn through line 11 for further processing, as hereinabove described.

A bottoms stream is withdrawn from column 115 through line 121, with reboil being provided through line 122, and such bottoms stream in line 121 which contains allyl chloride, the extraction solvent and chlorinated $C_3$ byproducts is introduced into a column 123, designed and operated to separate chlorinated $C_3$ components which boil below allyl chloride.

Such chlorinated $C_3$ components, and in particular, monochloropropenes and mono-chloropropanes, are withdrawn as overhead through line 124, and passed through an overhead condenser 125 into a separator 126. Reflux requirements are provided through line 127, and net light chlorinated $C_3$ byproduct in line 128 is ultimately passed through line 24 for incineration, as hereinabove described.

A bottoms is withdrawn from column 123 through line 131, with reboil being provided through line 132, and such bottoms is introduced into a column 133, designed and operated to separate allyl chloride.

Allyl chloride overhead is withdrawn from column 133 through line 134 and passed through overhead condenser 135 into a separation vessel 136. Reflux is provided to column 133 through line 137 and net allyl chloride product is recovered through line 22.

Bottoms from column 133 in line 141, after providing reboil in line 142 is divided into two streams, with one of the streams, which is comprised essentially of 1,2-dichloropropane being employed as extraction solvent in line 103.

The other portion, in line 151 is introduced into a column 152 designed and operated to strip any lighter components therefrom, and in particular allyl chloride, which is recovered as overhead in line 103 for recycle to column 101.

Net bottoms from column 152, after providing reboil through line 155, which is recovered in 156 is eventually introduced into the waste incinerator 38 through line 24.

Thus, as should be apparent, in accordance with the present invention, the procedure for separating hydrogen chloride from a mixture containing hydrogen chloride and propylene is effectively incorporated into a process for producing allyl chloride by thermal chlorination of propylene.

Although the invention has been described with respect to a particular process for the production of allyl chloride, it is to be understood that the scope of the invention is not limited to such a process. Thus, the general teachings of the invention as to separation of hydrogen chloride from hydrogen chloride/propylene mixtures are applicable to other mixtures which contain hydrogen chloride and propylene.

The present invention is particularly advantageous in that it permits for effective separation of hydrogen chloride from a mixture of hydrogen chloride and propylene without significant reaction between the hydrogen chloride and propylene during such separation. In addition, the procedure of the present invention is capable of recovering hydrogen chloride from mixtures containing large portions of hydrogen chloride.

The above advantages and others should be apparent to those skilled in the art from the teachings herein.

Numerous modifications and variations of the present invention are possible in light of the above teachings and, therefore, within the scope of the appended claims, the invention may be practised otherwise than as particularly described.

We claim:

1. A process for separating hydrogen chloride from a mixture containing hydrogen chloride and propylene, comprising:

extractively distilling a mixture containing hydrogen chloride and propylene in the presence of an inert extraction solvent which boils above hydrogen chloride and propylene and which preferentially dissolves propylene to recover hydrogen chloride as light ends, and propylene and extraction solvent as heavy ends.

2. The process of claim 1 wherein the distillation temperature, pressure, extraction solvent and amount of extraction solvent are coordinated to prevent the presence of liquid hydrogen chloride during the distillation.

3. The process of claim 2 wherein the extraction solvent is comprised of at least one member selected from the group consisting of saturated hydrocarbons and chloro-substituted saturated hydrocarbons.

4. The process of claim 2 wherein the extractive distillation is effected at an overhead temperature of from $-100°$ F. to $70°$ F., a bottoms temperature of from $0°$ to $200°$ F. and a pressure of from 2 atm. absolute to 40 atm. absolute.

5. The process of claim 4 wherein the extraction solvent is comprised of dichloropropane.

6. In a process for producing allyl chloride by thermal chlorination of propylene wherein the reaction effluent is comprised of unreacted propylene, hydrogen chloride, allyl chloride and other chlorinated $C_3$ compounds, the improvement comprising:

extractively distilling said effluent in the presence of an inert extraction solvent which preferentially absorbs propylene and which boils above hydrogen chloride and propylene to recover hydrogen chloride as light ends and extraction solvent, propylene, allyl chloride and other chlorinated $C_3$ hydrocarbons as heavy ends.

7. The process of claim 6 wherein the distillation temperature, pressure, extraction solvent and amount of extraction solvent are coordinated to prevent the presence of liquid hydrogen chloride during the distillation.

8. The process of claim 7 wherein the extraction solvent is comprised of at least one member selected from the group consisting of saturated hydrocarbons and chlorosubstituted saturated hydrocarbons.

9. The process of claim 8 wherein the extractive distillation is effected at an overhead temperature of from $-100°$ F. to $70°$ F., a bottoms temperature of from $0°$ F. to $200°$ F. and a pressure of from 2 atm. absolute to 40 atm. absolute.

10. The process of claim 9 wherein the extraction solvent is comprised of dichloropropane.

11. The process of claim 1 wherein the extraction solvent is employed in an amount which is from 10 to 90 mole percent.

12. The process of claim 6 wherein the extraction solvent is employed in an amount of from 10 to 90 mole percent.

* * * * *